(12) United States Patent
Kelly

(10) Patent No.: US 6,450,664 B1
(45) Date of Patent: Sep. 17, 2002

(54) LINEAR ILLUMINATION UNIT HAVING PLURALITY OF LEDS

(75) Inventor: William Kelly, Cork (IE)

(73) Assignee: Stockeryale (IRL) Limited, Cork (IE)

( * ) Notice: Subject to any disclaimer, the term of this patent is extended or adjusted under 35 U.S.C. 154(b) by 16 days.

(21) Appl. No.: 09/676,772

(22) Filed: Oct. 2, 2000

(30) Foreign Application Priority Data

Oct. 1, 1999 (IE) .................................................. 990820

(51) Int. Cl.[7] .............................................. F21V 21/00
(52) U.S. Cl. ...................... 362/249; 362/244; 362/246; 362/294; 362/373; 362/218; 362/225; 362/800; 362/84
(58) Field of Search ................................ 362/249, 244, 362/245, 246, 294, 373, 218, 225, 223, 224, 800, 84

(56) References Cited

U.S. PATENT DOCUMENTS

| 4,814,667 | A | | 3/1989 | Tanaka | |
|---|---|---|---|---|---|
| 5,607,227 | A | | 3/1997 | Yasumoto et al. | |
| 5,632,551 | A | * | 5/1997 | Roney et al. | 362/249 |
| 5,813,753 | A | * | 9/1998 | Vriens et al. | 362/293 |
| 5,884,775 | A | | 3/1999 | Campbell | |
| 5,897,195 | A | * | 4/1999 | Choate | 362/33 |

FOREIGN PATENT DOCUMENTS

| EP | 0394999 A2 | 10/1990 |
|---|---|---|
| EP | 0560605 A1 | 9/1993 |
| WO | WO98/01746 | 1/1998 |
| WO | WO99/53238 | 10/1999 |

* cited by examiner

Primary Examiner—Sandra O'Shea
Assistant Examiner—Ronald E. DelGizzi
(74) Attorney, Agent, or Firm—Jacobson Holman, PLLC

(57) ABSTRACT

A linear illumination unit (30) has a line of unlensed LEDs (31) which emit light spreading out. The light is focused into a line by a Fresnel lens (33) which allows spread and mixing of light in the linear direction and limits spread in the orthogonal direction. A Fresnel lens is particularly effective for this purpose. The housings 34 have slots 36 to help control light spread, and the housings are open-ended to allow spread of light in the linear direction beyond the confines of the, geometry of the units. Thus, units (30) may be interconnected to provide seamless linear light in a modular manner.

14 Claims, 8 Drawing Sheets

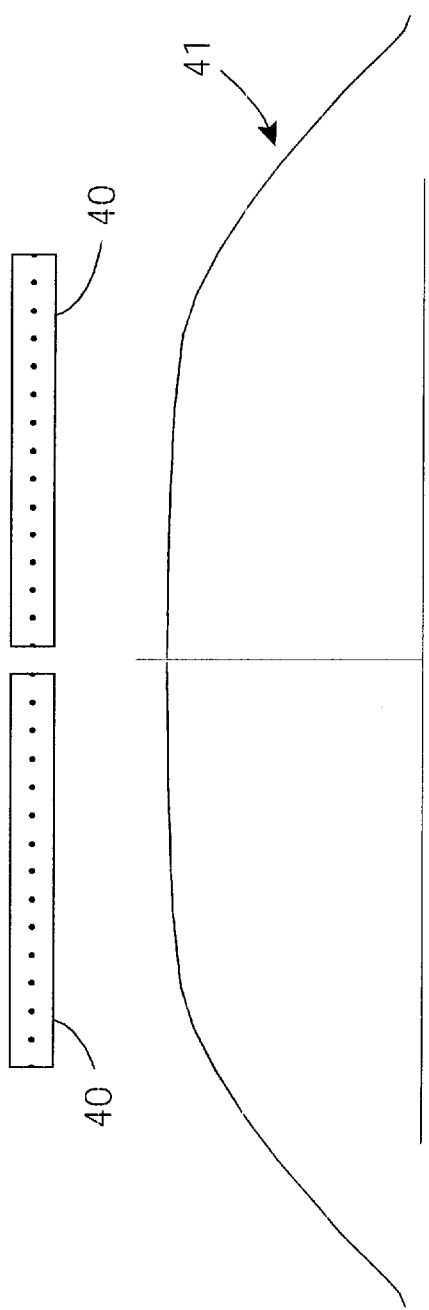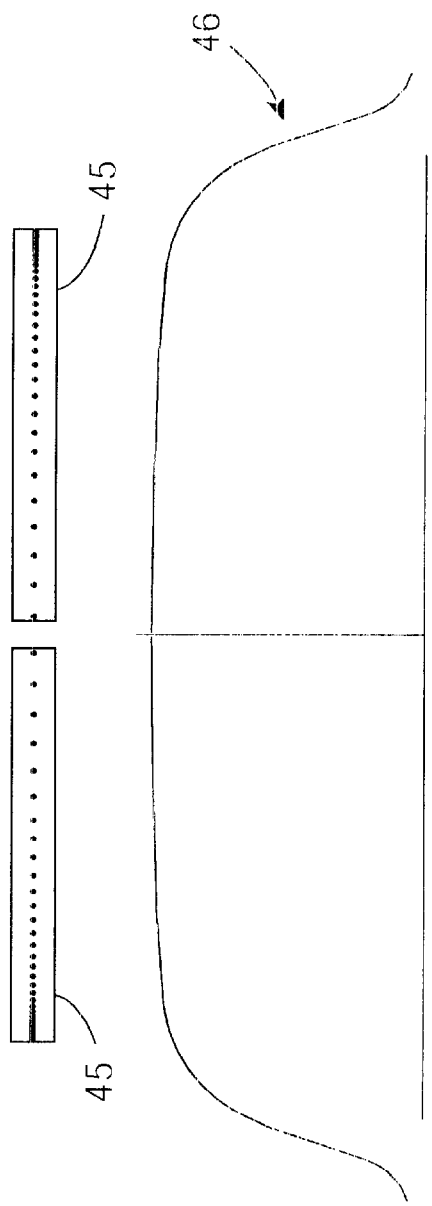

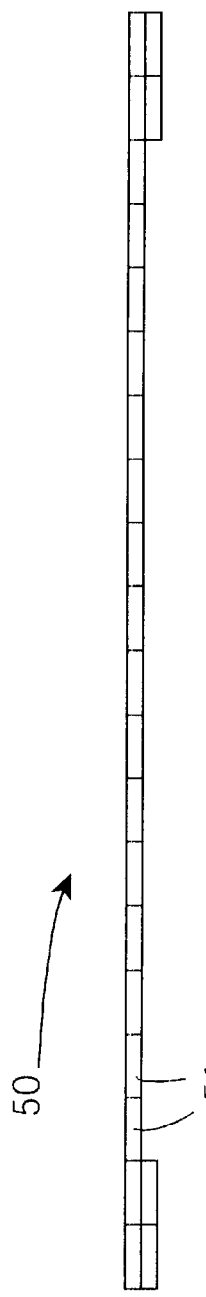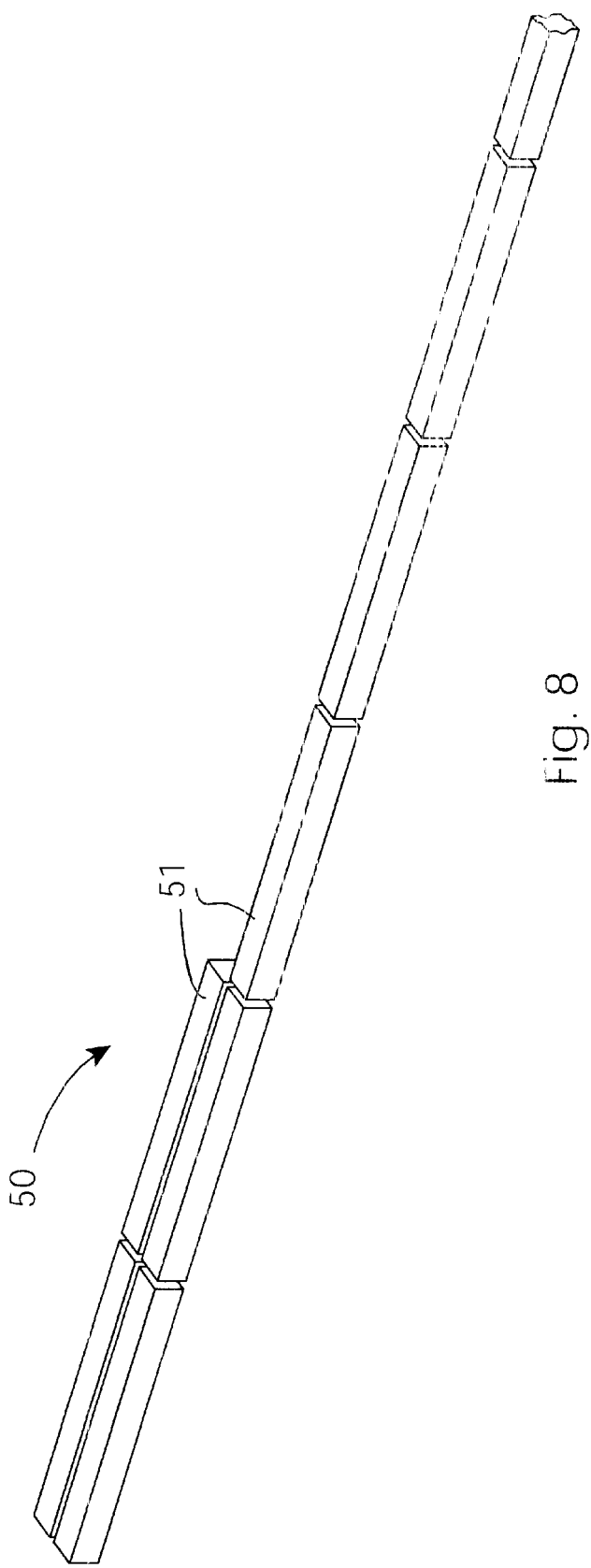

LINEAR ILLUMINATION UNIT HAVING PLURALITY OF LEDS

FIELD OF THE INVENTION

The invention relates to linear illumination. Such illumination is required, for example, for "web" applications in which items are conveyed on a web and are inspected by a camera. Typically, a linescan camera is used in this application. Since the linescan camera is inspecting a narrow strip of the web, transverse to its direction of motion, the requirement for the illumination source is that it illuminate the appropriate strip of material to the brightness level which is required. Exaiyiplics of web inspection are inspection of surfaces of ceramic tiles, print media, electronic components on printed circuit boards (PCBs), paper, and pharmaceutical packaging. It may also be used for sorting or grading of fruit and vegetables. Another application is scanners, in which the light source moves rather than the target.

PRIOR ART DISCUSSION

A typical machine vision system consists of an illuminator, a camera, and a control system for enabling the illuminator and camera in combination to capture an image of the object which is under inspection and for processing the image and initiaiting the desired action. The action may be marking the product as acceptable or rejected. The illuminator is an important part of the system, and properties of the illumination such as its brightness, its uniformity, its angle of incidence, its colour, and its degree of collimation can have a significant influence on the overall performance of the complete vision system. Additionally, the physical size of the illuminator is very important, as for some vision systems there is very little physical space available. For example, it may need to be located within a camera housing. Several types of illuminator have been used with machine vision systems, for example incandescent bulbs, fluorescent tubes, lasers, Xenon flash tubes, halogen bulbs combined with fibre light guides, and light emitting diodes (LEDs). Due to their relative cheapness, physically small size, long lifetime, fast switching speed and reasonable efficiency, LEDs have become increasingly popular.

In general linear illumination applications require that the camera have a fast shutter speed to stop the motion adversely affecting the image which is processed. Also, these applications require good intensity uniformity, ideally better than +/−5% along the line. A further requirement is a minimum intensity of illumination. This latter parameter depends upon factors such as the speed of the web, and typical mid-speed applications require at least 10 W/m$^2$.

Heretofore, such illumination has been provided by light sources such as a halogen lamp or a gas discharge/fluorescent lamp (WO9801746 and U.S. Pat. No. 5,884,775). Such light sources are generally expensive to install and to maintain and a further problem is that they are quite bulky. Illumination has also been provided by lighting heads connected to halogen or other fibre-coupled sources. Such light sources are also quite bulky and expensive, and suffer from limited source lifetime and other problems.

Another type of linear illuminator consists of an arrangement of light emitting diodes arranged either within a housing, or on a printed circuit board within a housing. Each LED is in its own lensed package with a particular viewings angle. By viewing angle is meant the full width angle measurement in the far field at the half power points of the light which is being emitted from the package. In general, the light from these packages has a cross-sectional profile which is such that it can not be described by a smooth mathematical function such as a Gaussian function, but has undesirable intensity variations caused by the structure of the LIED chip and/or by the arrangement of the LED within the optical elements of the package. There is the potential for a lot of structure (non-uniformity) in the illumination pattern which is produced when these packaged LEDs are used to make an illuminator depending upon how well the beams from the individual LEDs mix. This can be improved by adding diffuser material either within the individual LED packages or on the exterior of the housing of the illuminator, but the effect in both circumstances is to reduce the efficiency of the system. The overall volume of the illuminator is very much determined by the size of the individual diode packages, which are typically several millimetres in diameter.

A problem with such illuminators is that the pointing accuracy of individual LEDs is poor, leading to lack of uniformity of the illuminated area. Also, the uniformity of the light produced by the individual LEDs is poor, and even after they mix on the target, the resulting uniformity is poor, perhaps +/−25%. Another disadvantage is that the overall brightness of the illumination is limited by the packing density of the individual packaged LEDs, which are typically housed in 5 mm or 3 mm diameter acrylic packages. For example, a 100 mm long line illuminator can include between 20 and 40 of these LEDs. Therefore, it is an object of the invention to provide a line illuminator which has some or all of the following advantages:

- is compact, providing a high ratio of brightness to illuminator volume,
- provides a uniform illumination intensity over the desired target area,
- incorporates redundancy so that failure of some source!; does not result in darker areas within the illuminated area,
- has a relatively high optical efficiency,
- can be readily focused to adjust the size of the illuminated area,
- allows configuration for a required application at the design and/or installation stages in a versatile manner.

SUMMARY OF THE INVENTION

According to the invention, there is provided a linear illumination Unit comprising a plurality of light sources mounted on a housing in a linear direction, and a lens mounted to focus light emitted by the light sources to provide a line of light, characterized in that, the light sources are light emitting diodes having a viewing angle in excess of 60° whereby light is spread from the diodes to the lens and the lens allows spread in the linear direction and limits spread in a direction orthogonal to the linear direction.

In one embodiment, the light emitting diodes comprise an elongated mitting aperture extending in the linear direction.

In one embodiment, the light emitting diodes are integrated onto a monolithic integrated circuit.

In one embodiment, the light emitting diodes are covered by a continuous elongated body of epoxy.

In one embodiment, the epoxy contains a diffuser component.

In one embodiment, the epoxy contains a phosphor component.

In one embodiment, the illumination unit comprises a drive circuit for the light emitting diodes, the drive circuit comprising means for driving the light emitting diodes in groups each comprising distributed diodes whereby failure of a sub-circuit has a uniform impact on the illumination.

In one embodiment, the diodes adjacent to an end of the unit are more closely spaced than the other diodes.

In one embodiment, the lens is a Fresnel lens.

In one embodiment, the light emitting diodes are unlensed.

In one embodiment, the housing allows spread of light in the linear direction beyond the ends of the housing.

In one embodiment, the lens is mounted with respect to the light sources to allow light emitted by light sources of a neighboring illumination unit to enter the lens and be focused by it.

In one embodiment, the housing comprises means for mounting on a common support for a plurality of illumination units extending in the linear direction.

According to another aspect, there is provided a linear illumination system comprising a heat sink and a plurality of linear illumination units as described above mounted end-to-end in the linear direction on the heat sink.

According to another aspect, the invention provides a linear illumination unit comprising a plurality of light sources mounted on a housing in a linear direction, and a lens mounted to focus light emitted by the light sources to provide at line of light, characterized in that, the light sources are light emitting diodes having a viewing angle in excess of 60° whereby light is spread from the diodes to the lens and the lens allows spread in the linear direction and limits spread in a direction orthogonal to the linear direction, the lens is a Fresnel lens, the Fresnel lens is mounted with respect to the light sources to allow light emitted by light sources of a neighboring illumination unit to enter the lens and be focused by it, and the housing comprises means for mounting on a common heat sink support for a plurality of illumination units extending in the linear direction.

DETAILED DESCRIPTION OF THE INVENTION

BRIEF DESCRIPTION OF THE DRAWINGS

The invention will be more clearly understood from the following description of some embodiments thereof, given by way of example only with reference to the accompanying drawings in which:

FIGS. 5 and 6 are diagrams showing illumination intensity distribution for different illumination units of the invention;

FIGS. 7 and 8 are plan and perspective views respectively of an alternative illumination unit of the invention;

DESCRIPTION OF THE EMBODIMENTS

Figure 1:
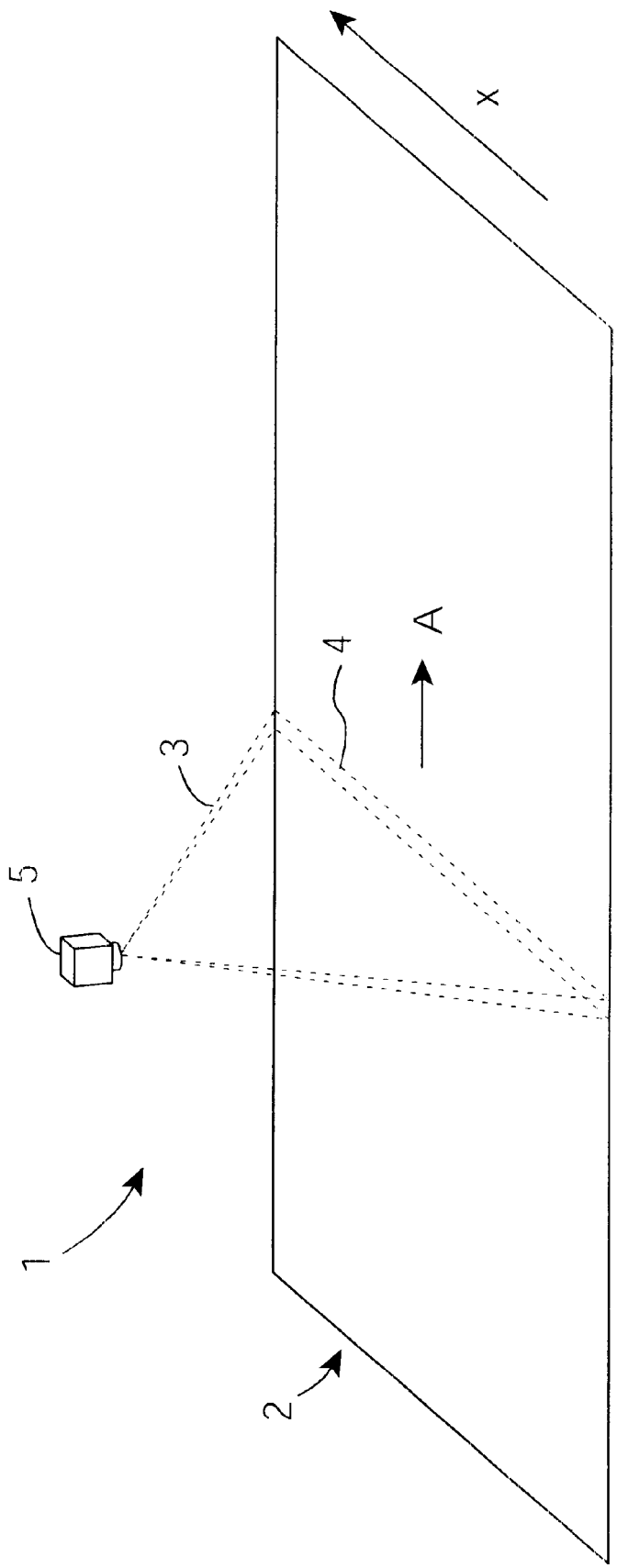
FIG. 1 is a diagrammatic perspective view of a web application showing the typical field of view of a linescan camera in relation to the web.

Referring to the drawings, and initially to FIG. 1 there is shown a diagrammatic perspective view of a web application showing the typical field of view of a linescan camera in relation to the web. A web 2 moves in the direction of the arrow A and conveys items which are being inspected. The web is inspected by a camera, typically a linescan camera 5, or an array of linescan or other cameras. The field of view of the camera or cameras is typically a long (several hundred millimetres up to tens of metres) narrow ( several millimetres or less) strip or line 4. The direction along the line, the linear direction, is shown as the x axis on FIG. 1.

Figure 2:
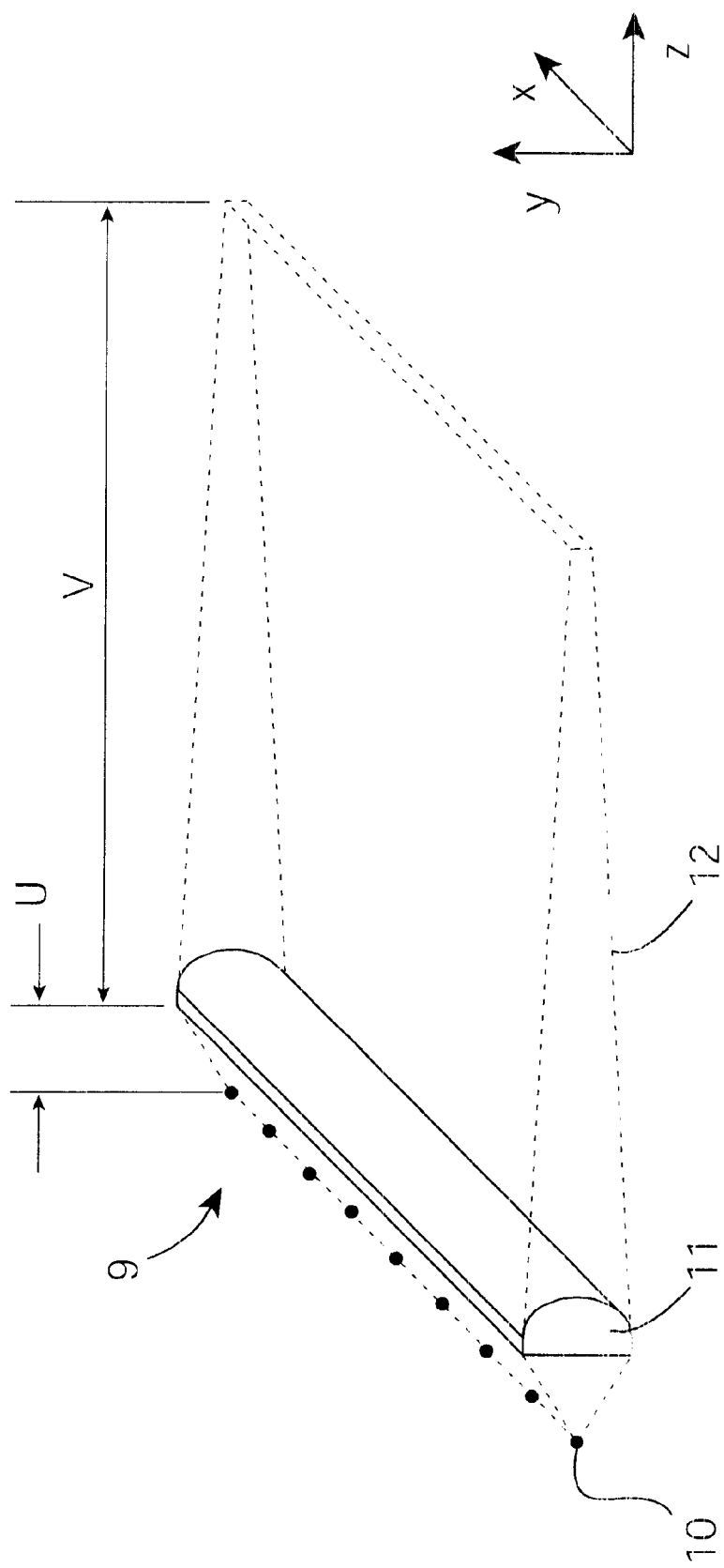
FIG. 2 is a diagrammatic perspective view showing operation of an illumination unit of the invention.

Referring now to FIG. 2 a lighting unit 9 of the invention is illustrated in diagrammatic form. A source of light 10 emits light which is focused by a cylindrical lens 11 to provide a projected line of light 12. The key spacing parameters are "u" which is the separation between the source 10 and the lens 11 and "v" which is. the distance between the lens 11 and the target upon which the light 12 impinges as a line. In the yz plane, the degree of divergence can be determined in the well understood way by application of the established thin-lens equations or other appropriate equations.

Figure 3:
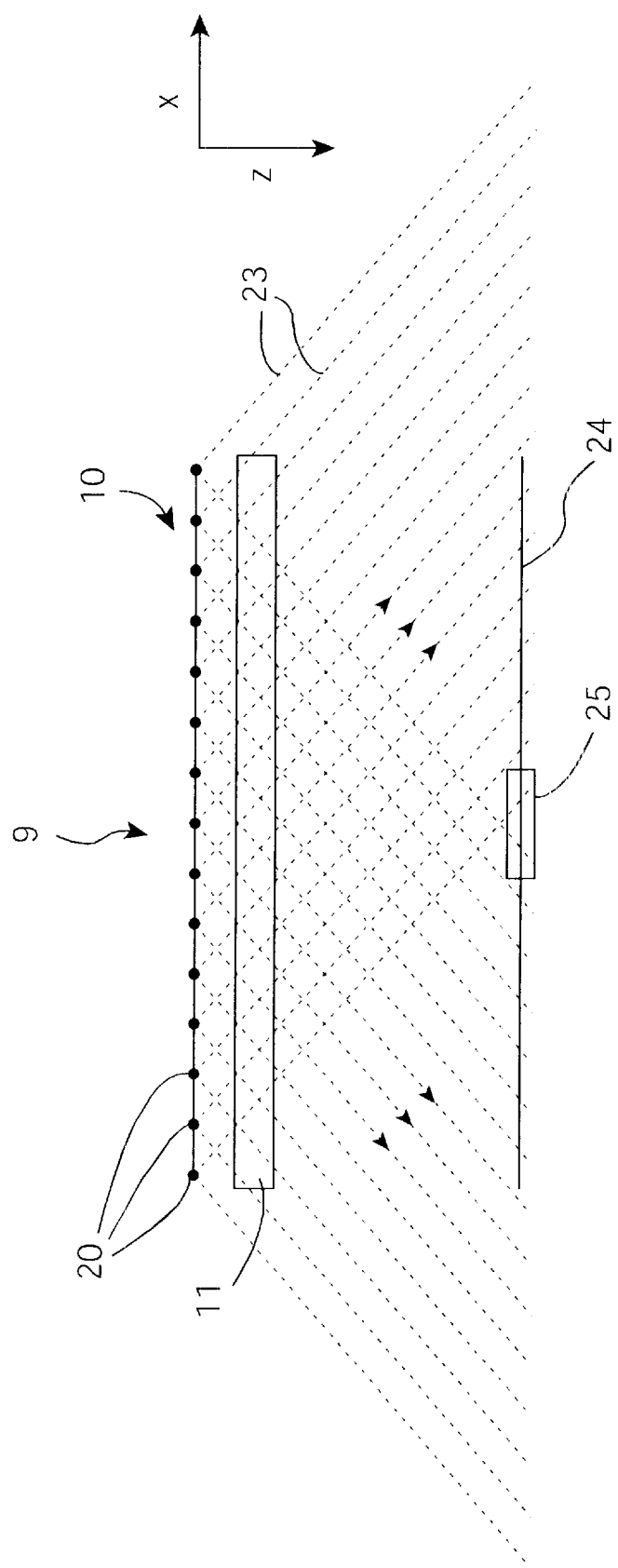
FIGS. 3 and 4 are diagrammatic front views, transverse to the direction of motion of the web.

As shown in FIG. 3, the source 10 comprises unlensed semi-conductor chip LEDs 20 of the type which emit light diverging approximately equally in all directions orthogonal to the centreline of propagation (z). Because the LEDs 20 are unlensed, the viewing angle is approximately 120°. However lensed LEI)s hiving a viewing angle greater than 60° may be used. The divergence in the xz plane, which includes the linear direction required by the web, is allowed by the lens 11 to remain unfocussed. This has a significant advantage for web applications as explained below. The divergence in the yz plane is focused by the cylindrical lens 11 so as to obtain a narrow bright line of illumination as required. Thus, as shown clearly in FIG. 3 individual beams 23 overlap to a very large extent at the web target 24 and any individual area of the target 24 such as the area 25 is illuminated by a number of LEDs 20. Also, because the LEDs 20 are semiconductor chips they are mounted much more densely than has previously been the case and in this embodiment the density is approximately 25 per cm, with typical chip sizes of 0.25 mm square.

It is also possible to arrange the chips in parallel lines, the effect being to then approximate a single thicker brighter line of chips. These techniques provide an illumination intensity (irradiate) of approximately 200 W/m$^2$ into a 5 mm wide line at a working distance of 100 mm with a single row of efficient 645 nm LED chips. With other chips, parallel lines and/or tighter focusing, significantly higher irradiances can be achieved.

These parameters provide adequate illumination intensity at the target 24 and because of the large overlap there is excellent uniformity, better than +/−5%.

Figure 4:
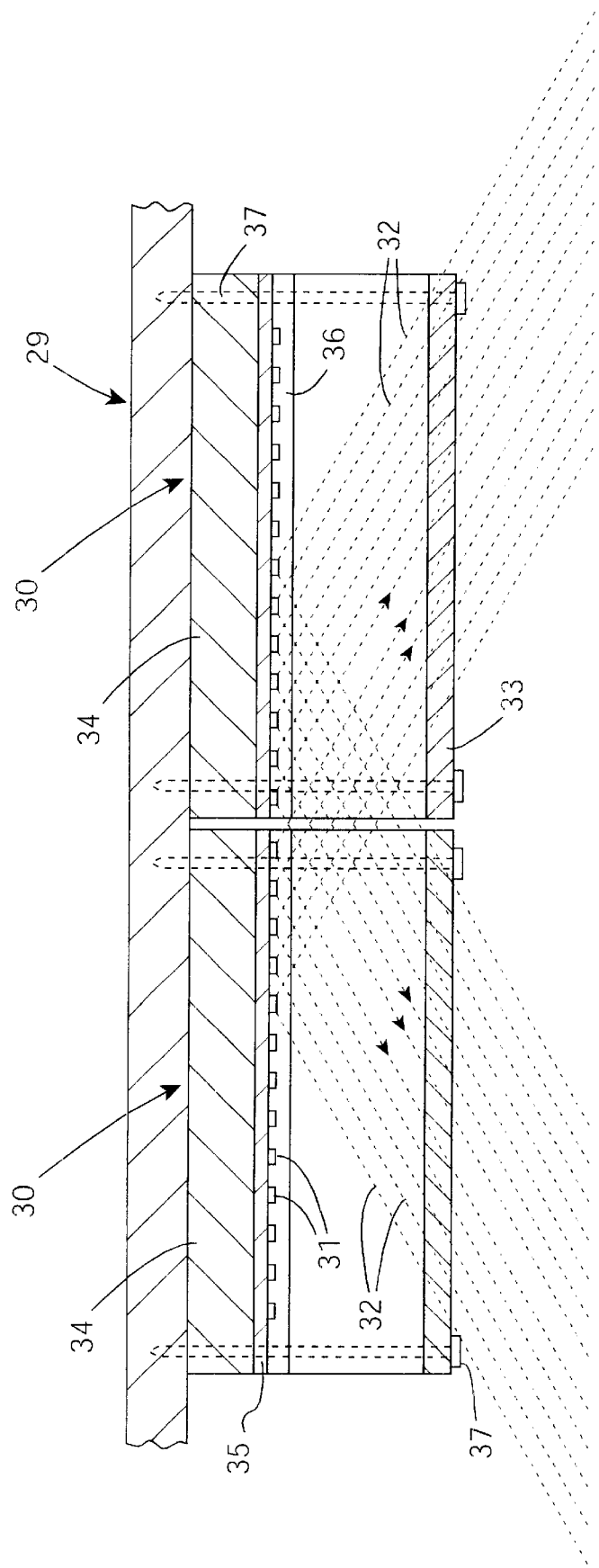

It will be apparent from FIG. 3 that a number of illumination units may be mounted alongside each other in the linear direction to extend the length of the line in a modular manner. Referring to FIG. 4, a heat sink 29 supports a number of illumination units 30 using fastening screws 37. These units 30 comprise LEDs 31 emitting beams 32 which are focused by a Fresnel lens 33. Because the ends of each unit 30 are open to allow linear (x-direction) spread of light there is seamless interconnection of the units. Thus, the line of illumination may be any desired multiple of the length of a single unit 30. The interconnection of the units 30 is made possible by the construction of housings 34 supporting the LED substrate 35. They comprise a flat abutment surface at each end, at which a slot 36 is open. The arrangement of FIG. 4 involves each Fresnel lens 33 focusing light emitted by LEDs 31 of a neighboring unit 30. This contributes to the uninterrupted, seamless nature of the illumination. The lack of mechanical side-structure allows the units to be mounted in sequence in the linear direction—with or without gaps separating them. The choice of gap depends on the application, and factors such as the working distance are important considerations when developing a system comprising the units and the heat sink.

The end-to-end mounting provides excellent versatility. Any required number of units may be mounted to provide the extent of illumination required for any particular application. Uniformity can be characterized as local, meaning over distances of the order of millimetres, or extended, meaning along the full width of the web, possibly several metres or more. Local uniformity of this illumination is excellent, as shown in FIG. 5, due to the mixing of the light from individual LEDs described above. In this drawing, a pair of side-by-side illumination units 40 provide an intensity distribution 41 which also has adequate extended uniformity (approximately 20% falloff at the edge of the line is shown in FIG. 5) for the physical length of the unit 40. Although the local uniformity is always excellent, the extended uniformity depends upon the working distance (from the unit to the web surface) and upon the length of the entire line of light (the width of the web). For narrow webs (short illuminated lines), the extended uniformity can be improved to the level which is required by mounting the LEDs more densely at the opposed ends as shown in FIG. 6. In this embodiment there is a pair of illumination units 45 in which the LEDs are more densely packed towards the ends to provide an improved extended uniform distribution 46. Alternatively, excellent uniformity with use of multiple units can be achieved by adding additional units which provide a line which is longer than that which is required for the web target area. A still further approach is to mount additional lighting units at the ends in a direction perpendicular to the linear direction, as shown in FIGS. 7 and 8. In these drawings, there is shown an illumination head 50 comprising multiple illumination units 51 mounted in a line and the units are doubled up at the ends to ensure there is sufficient intensity at the ends of the line.

It has been found that a Fresnel lens is particularly effective for an illumination unit of the invention. Fresnel lens are conventionally regarded as inferior to other lenses because the geometry of the surface causes aberrations with a de-focusing effect and efficiency loss. However, when a Fresnel lens is used to focus light from multiple densely-packed light sources for linear illumination, these features actually help to achieve greater mixing and uniform distribution of light in the linear (X) direction. The microscopic-level aberrations or random surface defects perform at useful function in smearing out some detail and improving uniformity.

Figure 9:
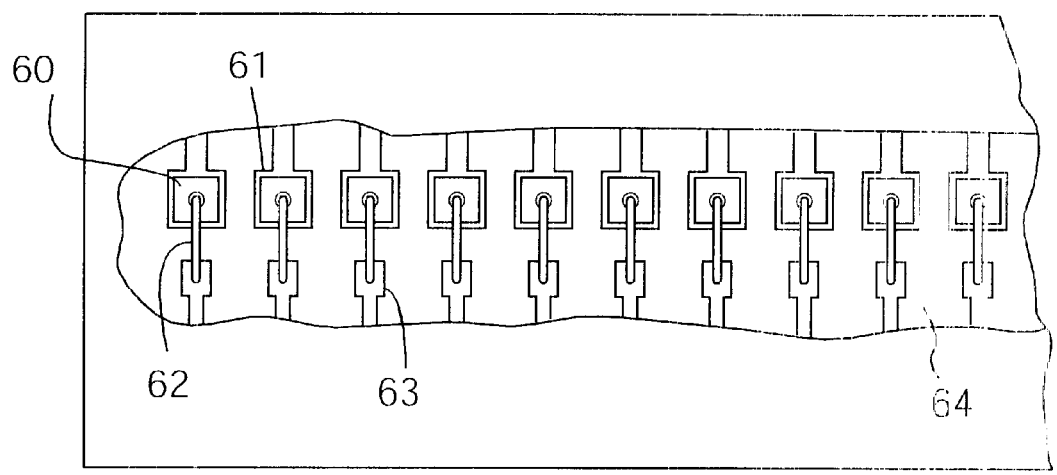
FIG. 9 is a plan view of an array of light source diodes.
Figure 10:
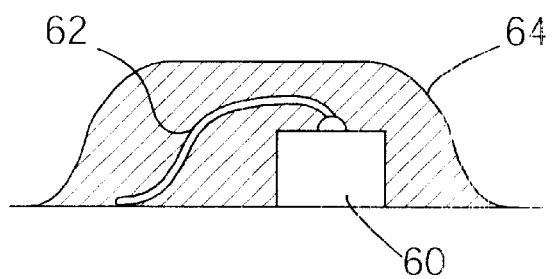
FIG. 10 is a diagrammatic cross-sectional view of an individual diode of this array.

Referring to FIG. 9, an array of LEDs 60 is illustrated. The LEDs 60 are mounted on metallised pads 61 and are driven by wire bonds 62. For clarity, only part of the PCB connector structure, such as pads and wire bonds, are illustrated in these diagrams. There is a continuous length of epoxy 64 over all the LEDs 60. This protects the LEDs. It includes a diffuser component in this embodiment small glass leads to improve uniformity. Alternatively or additionally, it may comprise a suspension of phosphorescent powder to adjust the spectral distribution of the light from the unit and to set the colour of the light. Use of a diffuser component and or a phosphor component has been found to be particularly effective at achieving uniformity along the linear direction. Additionally, the phosphor component sets the colour.

Figure 11:
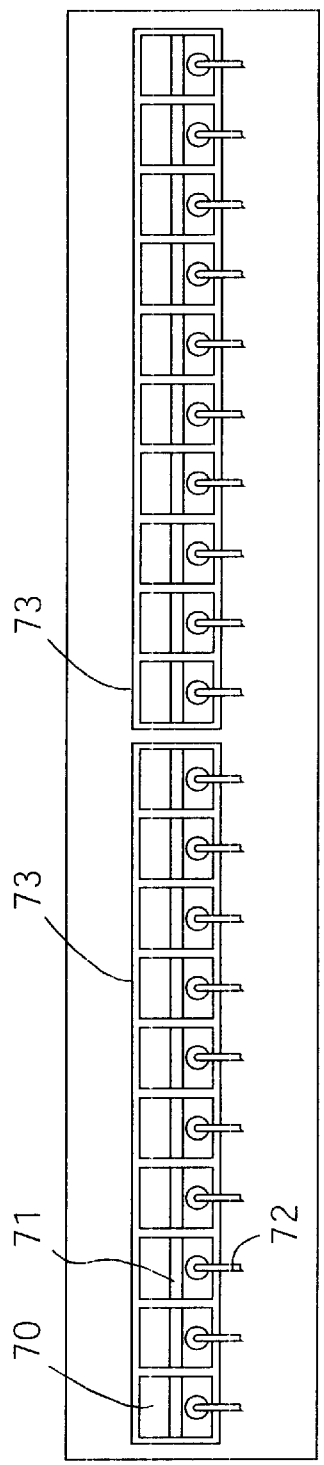
FIG. 11 is a plan view of a further array of diodes.
Figure 12:
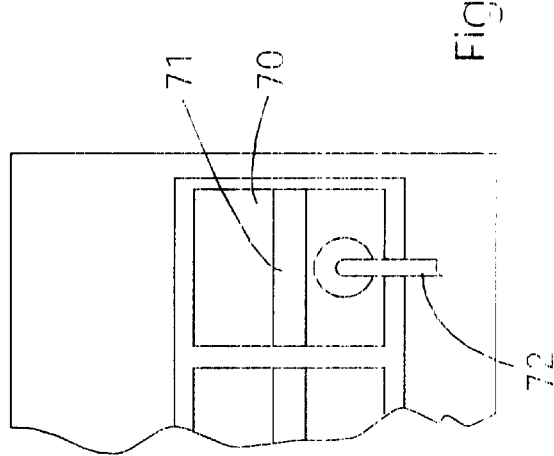
FIG. 12 is a plan view of an individual diode of this array.

Referring now to FIGS. 11 and 12, an array of LEDs 70 is illustrated. Each LED 70 comprises a central emitting aperture 71 driven by a bond 72. The emitting aperture may have an underlying diffused area in the semiconductor to block current from the non-apertured area of the chip, where the light would not be emitted from the chip. The aperture 71 is elongated in the linear direction to more closely approach the ideal of a long continuous light source. This embodiment has particular advantages also for inspection of specular objects in which the appearance of the source, as viewed in the specular surface of the object, should be as continuous as possible. The LED chips can be either individual LED chips, die attached to the substrate or PCB, or else, as shown in FIG. 1, they can consist of monolithic LED chips 73. FIG. 11 shows such chips 73 arranged side by side, each containing ten individual LEDs, such arrangement making possible an even smaller separation between the individual LEDs.

The operating temperature of an illumination unit of the invention is maintained at a relatively low level by using an aluminum housing with slotted !;ides to enhance the surface area. Also, high thermal conductivity ceramic boards and conductive paste are used to minimise thermal resistance between source and heat sink. Reliability is enhanced by driving the LEDs in groups. Each group comprises LEDs which are spaced-apart, for example, in a line of 100 chips arranged sequentially from locations 1 through 100. One group may comprise chips at locations, 1, 11, 21, etc. up to 91 and the next group would comprise chips at locations 2, 12, arid 22 etc. up to 92. Thus, if one circuit becomes inoperative because a chip has gone open circuit the effect is uniform along the length of the line.

It will be appreciated that the invention provides for use of LEDs for linear illumination in a manner which overcomes the traditional problems which have been associated with such use. There is excellent uniformity and brightness along the length of the line. There is also excellent versatility because of the manner in which units may be assembled together. Also, an illumination heat comprising one or more of the units is compact.

I claim:

1. A linear illumination unit comprising a plurality of light sources mounted on a housing in a linear direction, and a lens mounted to focus light emitted by the light sources to provide a line of light, the plurality of light sources include light emitting diodes having a viewing angle in excess of 60°, and light is spread from the diodes to the lens, and the lens allows spread in the linear direction and limits spread of the light in a direction orthogonal to the linear direction, the housing having open ends to permit spread of light in the linear direction beyond the open ends of the housing, and the lens is mounted with respect to the plurality of light sources to allow light emitted by a neighboring unit, and said neighboring unit having a plurality of light sources, and light emitted from said plurality of light sources enters and is focused by the lens.

2. The linear illumination unit as claimed in claim 1, wherein the light emitting diodes comprise an elongated emitting aperture extending in the linear direction.

3. The linear illumination unit as claimed in claim 1, wherein the light emitting diodes are integrated onto a monolithic integrated circuit.

4. The linear illumination unit as claimed in claim 1, wherein the light emitting diodes are covered by a continuous elongated body of epoxy.

5. The linear illumination unit as claimed in claim 4, wherein the epoxy contains a diffuser component.

6. The linear illumination unit as claimed in claim 4, wherein the epoxy contains a phosphor component.

7. The linear illumination unit as claimed in claim 1, wherein the illumination unit comprises a drive circuit for the light emitting diodes, the drive circuit having means for driving the light emitting diodes in groups, and each said group having sub-circuits with distributed diodes whereby failure of said sub-circuit of each said group has a uniform impact on the illumination.

8. The linear illumination unit as claimed in claim 1, wherein the diodes adjacent to one of said open ends of the unit are more closely spaced than other diodes of said plurality of light sources mounted on said housing.

9. The linear illumination unit as claimed in claim 1, wherein the lens is a Fresnel lens.

10. The linear illumination unit as claimed in claim 1, wherein the light emitting diodes are unlensed.

11. The linear illumination unit as claimed in claim 1, wherein the housing comprises means for mounting a common heat sink, said common heat sink supporting a plurality of illumination units extend in the linear direction.

12. The linear illumination system as claimed in claim 1 and further comprising a heat sink and a plurality of linear illumination units, each said linear illumination unit being mounted end-to-end in the linear direction on the heat sink.

13. A linear illumination unit comprising a plurality of light sources mounted on a housing in a linear direction, and a lens mounted to focus light emitted by the light sources to provide a line of light, said plurality of light sources having a plurality of light emitting diodes each diode having a viewing angle in excess of 60°, and light is spread from the diodes to the lens, and the lens allows spread in the linear direction and limits spread of the light in a direction orthogonal to the linear direction, the lens is a Fresnel lens, the Fresnel lens is mounted with respect to the light sources to allow light emitted by a neighboring illumination unit, and said neighboring illumination unit having a plurality of neighboring light sources, and light emitted from said plurality of light sources enters and is focused by the lens, and the housing having means for mounting a common heat sink, said common heat sink supporting a plurality of illumination units to extend in the linear direction.

14. A linear illumination system comprising a heat sink and a plurality of linear illumination units, each said linear unit including a plurality of light sources mounted on a housing in a linear direction, and a lens mounted to focus light emitted by the light sources to provide a line of light, each said plurality of light sources having a plurality of light emitting diodes each diode having a viewing angle in excess of 60°, and light is spread from the diodes to the lens, and the lens allows spread in the linear direction and limits spread of the light in a direction orthogonal to the linear direction, the lens is a Fresnel lens, and the Fresnel lens is mounted with respect to the light sources to allow light emitted by a neighboring illumination unit of said plurality of light sources, and said neighboring illumination unit having a plurality of neighboring light sources, and light emitted from said plurality of light sources enters and is focused by the lens, and the housing having means for mounting said heat sink, said heat sink supporting said plurality of illumination units to be mounted end-to-end in the linear direction on the heat sink.

* * * * *